United States Patent [19]

Miller et al.

[11] Patent Number: 4,551,572
[45] Date of Patent: Nov. 5, 1985

[54] PROCESS FOR REACTING AROMATIC COMPOUNDS

[75] Inventors: Jeffrey T. Miller, Naperville, Ill.; Albert L. Hensley, Jr., Munster, Ind.

[73] Assignee: Standard Oil Company (Indiana), Chicago, Ill.

[21] Appl. No.: 641,830

[22] Filed: Aug. 17, 1984

[51] Int. Cl.$^4$ .............................................. C07C 2/86
[52] U.S. Cl. .................................. 585/454; 585/467; 585/468
[58] Field of Search ....................... 585/454, 467, 468

[56] References Cited

U.S. PATENT DOCUMENTS

| 4,384,155 | 5/1983 | Chu | 585/467 |
| 4,409,412 | 10/1983 | Haag et al. | 585/468 |
| 4,423,265 | 12/1983 | Chu et al. | 585/322 |
| 4,487,983 | 12/1984 | Miller et al. | 585/454 |

*Primary Examiner*—Curtis R. Davis
*Attorney, Agent, or Firm*—James R. Henes; William T. McClain; Ralph C. Medhurst

[57] ABSTRACT

A process for reacting an aromatic compound, water and carbon monoxide in the presence of a cadmium-containing catalyst is disclosed.

18 Claims, No Drawings

PROCESS FOR REACTING AROMATIC COMPOUNDS

BACKGROUND OF THE INVENTION

1. Field of the Invention

This invention relates generally to the reaction between an aromatic compound, water and carbon monoxide, and more particularly concerns such reaction in the presence of a cadmium-containing catalyst.

2. Description of the Prior Art

The production from less valuable materials of aliphatic compounds boiling in the gasoline range, of aromatic compounds, and of intermediates useful for the production of such aliphatic and aromatic compounds, is highly desirable and has been the object of several prior art methods involving the use of cadmium-containing catalysts. For example, Miller and Nevitt, copending application Ser. No. 536,672, now U.S. Pat. No. 4,487,983, disclose a method for reacting an aromatic compound, hydrogen and at least one of carbon monoxide and an alcohol containing from 1 to 6 carbon atoms, at a temperature in the range of from about 300° C. to about 480° C., at a pressure in the range of from about 5 to about 150 kilograms per square centimeter, and in the presence of a catalyst composition comprising a cadmium component and a support material having acidic properties, wherein the cadmium component is in the form of the elemental metal, its oxide or salt or a combination thereof, and wherein the cadmium component is present at a concentration level in the range of from about 0.1 to about 20 weight percent, calculated as cadmium oxide and based on the weight of the catalyst. A disadvantage of the aforesaid method of Miller and Nevitt is that hydrogen from an external source must be employed.

Woodruff et al., U.S. Pat. Nos. 1,625,924 and 1,625,928, disclose a method for producing methanol by reacting oxides of carbon with hydrogen at high pressures and in the presence of a catalyst comprising one or more non-reducible metal oxides, such as zinc, magnesium, cadmium, chromium, vanadium, or tungsten, and one or more easily reducible metal oxides, such as copper, silver, iron, nickel, or cobalt, and a metallic halide. Melaven et al., U.S. Pat. No. 2,301,735, disclose a process for converting heavy hydrocarbon oils into gasoline by contacting the heavy oils with a catalyst comprising silica impregnated with a cadmium compound.

Klotz, U.S. Pat. No. 4,269,813, discloses a crystalline borosilicate catalyst comprising a molecular sieve material having the following composition in terms of mole ratios of oxides:

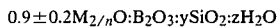

$$0.9\pm0.2 M_{2/n}O:B_2O_3:ySiO_2:zH_2O$$

wherein M is at least one cation, n is the valence of the cation, y is a value within the range of 4 to about 600, and z is a value within the range of 0 to about 160, and providing a specific X-ray diffraction pattern. M represents an alkali metal cation, an alkaline earth metal cation, an ammonium cation, an alkylammonium cation, a hydrogen cation, a catalytically active metal cation, or mixtures thereof. Klotz also discloses that the original cation "M" in the above formulation can be replaced by tetraalkylammonium cations, metal ions, ammonium ions, hydrogen ions, and mixtures thereof, particularly hydrogen, rare earth metals, aluminum, metals of Groups IB, IIB and VIII of the Periodic Table, noble metals, manganese, and other catalytically-active materials and metals known to the art. The catalytically-active components can be present at concentrations from about 0.05 to about 25 weight percent of the crystalline borosilicate. Klotz discloses that the crystalline borosilicate can be employed effectively as a catalyst for various processes including reforming, hydrocracking, transalkylation, disproportionation, isomerization, and alkylation, and is particularly suitable for the isomerization of xylenes, the conversion of ethylbenzene and the conversion of alcohols, such as methanol, to useful products, such as aromatics or olefins.

Fraenkel et al., U.S. Pat. No. 4,294,725, disclose a Fischer-Tropsch catalyst comprising a particulate synthetic zeolite incorporating a transition metal reduced in situ by a preselected vaporous reductant metal and a method of making the catalyst. In the disclosed method for making the catalyst, at least one reducible transition metal is incorporated by ion exchange into a particulate synthetic zeolite catalyst support having ion-exchange properties, and the transition metal is then reduced with a vapor of at least one reductant metal having a reduction potential greater than the reduction potential of the transition metal. In one specific embodiment disclosed, cadmium is disclosed as a reducing metal which is present along with a transition metal in the final catalyst produced. Depending upon the conditions employed, saturated and unsaturated hydrocarbon products containing from one to five carbon atoms and an unidentified oxygenated product were produced when a catalyst containing cobalt as the transition metal and cadmium as the reducing metal was employed.

Chu, U.S. Pat. No. 4,384,155, discloses a process for the conversion of aromatic compounds, either alone or in admixture with a suitable alkylating agent, such as methanol or ethylene, to dialkylbenzene compounds which are rich in the 1,4-dialkylbenzene isomer, in the presence of a particular type of zeolite catalyst having a silica-to-alumina mole ratio of at least 12 and a constraint index of about 1–12, and containing a minor proportion of cadmium deposited thereon.

In addition, cadmium-containing catalysts have been employed in other unrelated methods. For example, Wietzel et al., U.S. Pat. No. 1,562,480, disclose a method for synthesizing higher molecular weight organic compounds containing oxygen by reacting an aliphatic alcohol with carbon monoxide and optionally with hydrogen at a temperature of at least about 400° C. and in the presence of the catalyst comprising both hydrogenating and hydrating constituents. Suitable hydrogenating constituents are disclosed as including copper, silver, gold, tin, lead, antimony, bismuth, zinc, cadmium and thallium, and suitable hydrating constituents are disclosed as including titanium, zirconium, thorium, vanadium, niobium, manganese, cerium, lanthanum, tantalum, chromium, molybdenum, tungsten, uranium, didymium, glucinium and aluminum.

Perkins et al., U.S. Pat. No. 2,107,710, disclose a method for hydrolyzing a halohydrocarbon in the vapor phase and in the presence of a catalyst comprising silica gel impregnated with one or more salts of metals belonging to the Groups IIB, IIIB, IVA or B, or VB of the periodic system, for example, beryllium nitrate, magnesium sulfate, zinc sulfate, cadmium nitrate, boron fluoride, aluminum chloride, stannous chloride, lead nitrate, titanium tetrachloride, antimony nitrate or bismuth chloride.

La Lande, U.S. Pat. No. 2,395,931, discloses a decolorizing adsorbent or catalyst comprising a water-insoluble metal aluminate formed by the reaction in aqueous solution of an alkali metal aluminate and a water-soluble salt of a metal capable of forming a water-insoluble metal aluminate in the presence of a compound yielding ammonium ions. Suitable water-soluble salts of metals capable of forming a water-insoluble metal aluminate include the chlorides or sulfates of magnesium, calcium, or aluminum, and soluble salts of strontium, barium, lead, copper, cadmium, iron, chromium, cobalt, nickel, manganese, thorium, cerium, beryllium, molybdenum, tin, titanium, zirconium, tungsten and vanadium. The catalyst is disclosed for use in decolorizing hydrocarbon oils.

Mecorney et al., U.S. Pat. No. 2,697,730, disclose a catalyst comprising one or more metals, such as copper, silver, chromium, manganese, nickel, tungsten, cobalt, iron, cadmium, uranium, thorium, tin or zinc, either in the form of the elemental metals, their oxides, hydroxides, or salts, wherein the metal component is supported on activated alumina or diatomaceous earth. The catalyst is disclosed for use in synthesizing higher ketones.

Cislak et al., U.S. Pat. No. 2,744,904, disclose a process for preparing pyridine and 3-picoline by reacting acetylene, ammonia and methanol in the presence of a catalyst comprising activated alumina impregnated with cadmium fluoride.

Finch et al., U.S. Pat. No. 2,763,696, disclose a method for reducing alpha- or beta-olefinic aldehydes or ketones to the corresponding alpha- or beta-unsaturated alcohols by direct hydrogenation of the aldehydes or ketones in the vapor phase and in the presence of a catalyst comprising elemental cadmium, its oxide, or a mixture thereof, and one or more additional metals known to have hydrogenating-dehydrogenating characteristics, such as a heavy metal selected from the first, second, sixth or eighth groups of the Periodic Table of the Elements. These metal components of the catalyst are disclosed as being employed either in the unsupported state or as supported on a suitable carrier, such as silica, alumina, kieselguhr or other diatomaceous earth material, pumice or the like.

Pearson et al., U.S. Pat. No. 3,725,531, disclose a process wherein industrial off-gases containing organic sulfur components are contacted with an alumina base catalyst to convert these organic sulfur components to easily removable compounds, such as carbon dioxide and elemental sulfur. The catalyst employed comprises an alumina base support in combination with at least one metal selected from strontium, calcium, magnesium, zinc, cadmium, barium and molybdenum.

Eurlings et al., U.S. Pat. No. 3,862,055, disclose a method for the preparation of a catalyst system having a catalytically-active component of an oxide, metal or alloy of any one or more of copper, zinc, cadmium, nickel, cobalt, iron, manganese or magnesium, homogeneously dispersed over a solid particulate inorganic thermostable carrier material. Suitable inorganic thermostable materials, for use as the carrier, are disclosed generally as including synthetic or mineral carrier materials, such as alumina or silica.

Eberly, U.S. Pat. No. 4,358,297, discloses a process wherein a particulate sorbent mass of zeolite, which has been ion-exchanged with zinc or cadmium to provide pore size openings of at least about 5 angstroms, is contacted with a moist hydrocarbon process stream which contains sulfur, sulfur compounds, and other contaminants, these being adsorbed onto the particulate sorbent mass.

Mathe et al., U.S. Pat. No. 4,361,500, disclose a process for the preparation of a supported metal catalyst containing at least one metal belonging to Group A and optionally at least one metal belonging to Group B, wherein Group A encompasses palladium, rhodium, ruthenium, platinum, iridium, osmium, silver, gold and cadmium, and Group B encompasses zinc, mercury, germanium, tin, antimony and lead. This patent discloses that any of the known substances commonly used as supports for catalysts can be used as a support in the catalyst disclosed, and the following supports are specifically mentioned: activated carbons, aluminum oxides, silicon dioxides, aluminosilicates and various molecular sieves, and barium sulfate. The catalyst is disclosed for use in hydrogenation reactions.

OBJECTS OF THE INVENTION

It is a general object of the present invention to provide a method for the direct production of more valuable aromatic compounds from less valuable aromatic compounds.

More particularly, it is an object of the present invention to provide a single-step method for the direct production of alkylated aromatic compounds.

It is a further object of the present invention to provide a single-step method for the direct and highly selective production of p-xylene and pseudocumene.

It is a related object of the present invention to provide a single-step method for the direct production of more valuable aromatic compounds from less valuable aromatic compounds employing a catalyst having improved activity maintenance.

Other objects and advantages of the invention will become apparent upon reading the following detailed description and appended claims.

SUMMARY OF THE INVENTION

The present invention is a method for reacting an aromatic compound, water and carbon monoxide, at a temperature in the range of from about 300° C. to about 480° C., at a pressure in the range of from about 5 to about 150 kilograms per square centimeter, and in the presence of a catalyst composition comprising a cadmium component and a support material having acidic properties. The cadmium component is in the form of the elemental metal, its oxide or salt or a combination thereof, and is present at a concentration level in the range of from about 0.1 to about 20 weight percent, calculated as cadmium oxide and based on the weight of the catalyst.

DETAILED DESCRIPTION

Catalysts suitable for use in the method of this invention comprise a cadmium component and a support material having acidic properties. The cadmium component can be present either as a component deposited on the support or as a component formed from cadmiun ions exchanged into the support replacing exchangeable cations in the support. The cadmium component is in the form of elemental cadmium, its oxide or salt or a combination thereof, and is present at a concentration level in the range of from about 0.1 to about 20 weight percent, calculated as cadmium oxide and based on the weight of the catalyst. Preferably, the cadmium component is present at a concentration level of from about 1 to about 10 weight percent, calculated as cadmium oxide and based on the weight of the catalyst. The cadmium component is preferably in the form of cadmium oxide.

Preferably, the catalyst additionally comprises a thorium component. The thorium component has essentially no catalytic activity itself in the method of this invention, but serves to promote the catalytic activity of the cadmium component. Like the cadmium component, the thorium component can be present either as a component deposited on the support or as a component of the support formed from thorium ions exchanged into the support replacing exchangeable cations in the support. In addition, a thorium component can be a component of the support formed by admixture of a thorium component with an amorphous refractory inorganic oxide, such as alumina, silica or silica-alumina. The thorium component is in the form of elemental thorium, its oxide or salt or a combination thereof, and is present at a concentration level in the range of from about 1 to about 25 weight percent, calculated as thorium oxide and based on the weight of the catalyst. Preferably, the thorium component is present at a concentration level of from about 3 to about 15 weight percent, calculated as thorium oxide and based on the weight of the catalyst. The thorium component is preferably in the form of thorium oxide.

Any porous support material having acidic properties is suitable for use in the catalyst employed in the method of this invention. Thus, suitable supports comprise an amorphous refractory inorganic oxide, a molecular sieve, a pillared smectite or vermiculite clay, or a combination thereof. Refractory inorganic oxides having acidic properties typically comprise alumina, zirconia, titania, an oxide of a metal of the lanthanide series, an oxide of a metal of the actinide series, a combination thereof, or a combination thereof with silica or magnesia. The amorphous refractory inorganic oxide can also include adjuvants, such as one or more oxides of phosphorus or boron, or a halogen, such as chlorine or fluorine.

The support material of the catalyst employed in the method of the present invention can also comprise a crystalline molecular sieve containing exchangeable cations and can be in the unexchanged or cation-exchanged form. A suitable molecular sieve comprises a crystalline aluminosilicate, crystalline borosilicate or a combination thereof. A suitable crystalline aluminosilicate includes chabazite, clinoptilolite, erionite, mordenite, zeolite A, zeolite L, zeolite X, zeolite Y, ultrastable large-pore zeolite Y, zeolite omega, or a ZSM-type zeolite such as ZSM-5, ZSM-11, ZSM-12, ZSM-35, ZSM-38 or ZSM-48.

Mordenite-type crystalline aluminosilicates have been discussed in the patent art, for example, in Kimberlin, U.S. Pat. No. 3,247,098; Benesi et al., U.S. Pat. No. 3,281,483; and Adams et al., U.S. Pat. No. 3,299,153. Those portions of each of these patents that are directed to mordenite-type aluminosilicates are specifically incorporated by reference herein. Synthetic mordenite-type crystalline aluminosilicates, designated as Zeolon, are available from the Norton Company of Worcester, Mass.

One example of a crystalline molecular sieve that is suitable for use in the support of the catalyst employed in the method of the present invention is an unexchanged high sodium content, Y-type zeolitic crystalline aluminosilicate, such as the sodium-Y molecular sieve, designated as Catalyst Base 30-200, and obtained from the Linde Division of Union Carbide Corporation.

Another example of a crystalline molecular sieve that can be employed in the support of the catalyst employed in the method of the present invention is a metal-exchanged, Y-type molecular sieve. Y-type, zeolitic molecular sieves are discussed in U.S. Pat. No. 3,130,007. The metal-exchanged, Y-type molecular sieve can be prepared by replacing the original cation associated with the molecular sieve by a wide variety of other cations according to techniques that are known in the art. Ion-exchange techniques have been disclosed in many patents, several of which are U.S. Pat. Nos. 3,140,249; 3,140,251; and 3,140,253. Specifically, a mixture of rare earth metals can be exchanged into a Y-type zeolitic molecular sieve, and such rare earth metal-exchanged, Y-type molecular sieves can be employed suitably in a support used in the catalyst employed in the method of the present invention. Specific examples of suitable rare earth metals are cerium, lanthanum, and praesodymium. In one particularly preferred embodiment, cadmium ions are exchanged into a Y-type zeolitic molecular sieve, with the result being that the cadmium component of the catalyst is a component of the catalyst support.

Ultrastable, large-pore, Y-type, zeolitic crystalline aluminosilicate material is described in U.S. Pat. Nos. 3,293,192 and 3,449,070. Each of these patents is specifically incorporated by reference herein. By large-pore material is meant a material that has pores which are sufficiently large to permit the passage thereinto of benzene molecules and larger molecules and the passage therefrom of reaction products.

The ultrastable, large-pore, Y-type, zeolitic crystalline aluminosilicate material that is preferred for use in the support of the catalyst employed in the method of this invention exhibits a cubic unit cell dimension and hydroxyl infrared bands that distinguish it from other aluminosilicate materials. The cubic unit cell dimension of the preferred ultrastable, large-pore, crystalline aluminosilicate is within the range of about 24.20 angstroms to about 24.55 angstroms. The hydroxyl infrared bands obtained with the preferred ultrastable, large-pore, crystalline aluminosilicate material are a band near 3,745 cm$^{-1}$ (3,745±5 cm$^{-1}$), a band near 3,695 cm$^{-1}$ (3,690±10 cm$^{-1}$), and a band near 3,625 cm$^{-1}$ (3,610±15 cm$^{-1}$). The band near 3,745 cm$^{-1}$ may be found on many of the hydrogen-form and de-cationized aluminosilicate materials, but the band near 3,695 cm$^{-1}$ and the band near 3,625 cm$^{31\ 1}$ are characteristic of the preferred ultrastable, large-pore, Y-type, zeolitic crystalline aluminosilicate material that is used in the catalyst of the present invention. The ultrastable, large-pore, Y-type, zeolitic crystalline aluminosilicate material is also characterized by an alkaline metal content of less than 1%.

Other molecular sieve materials that are useful in the support of the catalyst employed in the method of the present invention are ZSM-type crystalline aluminosilicate molecular sieves. Suitable crystalline aluminosilicates of this type typically have silica-to-alumina mole ratios of at least about 12:1 and pore diameters of at least 5 angstroms. A specific example of a useful crystalline aluminosilicate zeolite of the ZSM-type is ZSM-5, which is described in detail in U.S. Pat. No. 3,702,886. Other crystalline aluminosilicate zeolites of the ZSM-type contemplated according to the invention include ZSM-11, which is described in detail in U.S. Pat. No.

3,709,979; ZSM-12, which is described in detail in U.S. Pat. No. 3,832,449; ZSM-35, which is described in U.S. Pat. No. 4,016,245; and ZSM-38, which is described in detail in U.S. Pat. No. 4,046,859. All of the aforesaid patents are incorporated herein by reference. A preferred crystalline aluminosilicate zeolite of the ZSM-type is ZSM-5.

An additional molecular sieve that can be used in the catalytic composition of the present invention is a crystalline borosilicate, which is described in U.S. Pat. No. 4,269,813, which patent is specifically incorporated herein by reference. A suitable crystalline borosilicate is a molecular sieve material having the following composition in terms of mole ratios of oxides:

$$0.9 \pm 0.2 M_{2/n}O:B_2O_3:ySiO_2:zH_2O$$

wherein M is at least one cation having a valence of n, y is within the range of 4 to about 600, and z is within the range of 0 to about 160, and providing an X-ray pattern providing the following X-ray diffraction lines and assigned strengths:

| d Angstroms | Assigned Strength |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

M can be a cadmium ion, and thus the cadmium component can be incorporated into the crystalline borosilicate molecular sieve support itself, in addition to or instead of being deposited on the surface of the crystalline borosilicate molecular sieve support.

Suitable methods for preparing the aforesaid crystalline borosilicate molecular sieve are disclosed in Klotz, U.S. Pat. No. 4,269,813 and in Haddid, European Patent Application No. 82303246.1 which was published on Jan. 5, 1983.

Pillared smectite and vermiculite clays, which are also suitable for use in, or as, the support component of the catalyst employed in the method of this invention, are often referred to in the literature as pillared interlayered clays and occasionally as molecular sieves. The smectite clays comprise montmorillonite, beidellite, montronite, volchonskoite, hectorite, saponite, stevensite, sauconite and pimelite. Some pillared smectite and vermiculite clay materials that are suitable for use in the support of the catalyst employed in the method of this invention, and methods for preparing such clays, are disclosed in Vaughan et al., U.S. Pat. No. 4,176,090; Shabria et al., U.S. Pat. No. 4,216,188; Shabtai, U.S. Pat. No. 4,238,364; D'Aniello, U.S. Pat. No. 4,380,510; Pinnavaia, "Intercalated Clay Catalysts," Science, Vol. 220, pages 365–371 (Apr. 22, 1983); and Vaughan et al., "Preparation of Molecular Sieves Based on Pillared Interlayered Clays (PILC)," Fifth International Conference on Zeolites, pages 94–101 and in the references cited therein. Preferably, a suitable pillared smectite clay comprises a multiplicity of cations interposed between the molecular layers of the clay and maintaining the spacing between the molecular layers in the range of from about 6 angstroms to about 10 angstroms at a temperature of at least 300° C. in an air atmosphere for at least 2 hours.

Preferably, when the support comprises an aforesaid molecular sieve material or an aforesaid pillared smectite or vermiculite clay material or a combination thereof, the support also comprises an aforesaid amorphous refractory inorganic oxide. In such cases, the concentrations of the amorphous inorganic oxide and of the molecular sieve material and/or pillared smectite or vermiculite clay material are not critical. Preferably, the amorphous refractory inorganic oxide content is at least high enough to be effective to give the support sufficient strength and integrity so that the ultimate catalyst composition can be employed in the method of the present invention without appreciable damage to the catalyst. In such case, the total concentration of the molecular sieve material and/or pillared smectite or vermiculite clay material in such mixture is preferably from 5 to 90 weight percent, more preferably from 20 to 60 weight percent, based on the weight of the support, which support is made up of the amorphous refractory inorganic oxide and the molecular sieve material and/or the pillared smectite or vermiculite clay material.

Preferably, when the support comprises a mixture of a molecular sieve and/or pillared smectite or vermiculite clay and an amorphous refractory inorganic oxide, the support is in the form of a dispersion of the molecular sieve component and/or pillared smectite or vermiculite clay component in a matrix of the amorphous refractory inorganic oxide. Such dispersions can be prepared by well-known techniques, such as blending the molecular sieve component and/or pillared smectite or vermiculite clay component, preferably in finely-divided form, into a sol, hydrosol or hydrogel of the inorganic oxide, and then adding a gelling medium, such as ammonium hydroxide, and stirring to produce a gel. Alternately, the molecular sieve component and/or pillared smectite or vermiculite clay component is blended into a slurry of the amorphous inorganic oxide. In either case, the resulting mixture can be dried, shaped, if desired, and then calcined to form the final support component. A less preferred, but still suitable, method for preparing a suitable dispersion of the molecular sieve component and/or pillared smectite or vermiculite clay component in the inorganic oxide is to dry-blend particles of each, preferably in finely-divided form, and then to conduct any desired shaping operations, such as pelletizing or extrusion; the resulting mixture is then calcined.

The catalysts employed in the method of this invention can be prepared by impregnation of an aforesaid suitable support with at least one precursor of the cadmium component and optionally of the thorium component. Any convenient conventional impregnation technique can be employed for this purpose. For example, when the support comprises an amorphous refractory inorganic oxide, a soluble cadmium compound and, if a thorium component is to be present, a soluble thorium compound can be added to a sol or gel of the amorphous refractory inorganic oxide. This composition is thoroughly blended, and the sol or gel mixture is subsequently co-gelled by the addition of a dilute ammonia solution. The resulting co-gelled material is then dried and calcined. In another method of preparation, the refractory inorganic oxide is gelled, dried, calcined, and cooled, and the resulting material is then impregnated with one or more solutions of a cadmium compound and, if a thorium component is to be present, of a thorium compound.

When the support comprises both an amorphous refractory inorganic oxide and a molecular sieve and/or a pillared smectite or vermiculite clay, numerous convenient impregnation techniques can also be employed. For example, finely-divided molecular sieve material and/or pillared smectite or vermiculite clay material can be stirred into a sol or gel of a refractory inorganic oxide, and at least one soluble compound of cadmium—and optionally at least one soluble compound of thorium—is added to the sol or gel, followed by co-gelling of the sol or gel mixture by the addition of dilute ammonia. The resulting co-gelled material is then dried and calcined.

In another method of preparation, finely-divided molecular sieve material and/or pillared smectite or vermiculite clay material are mixed into a sol or gel of a refractory inorganic oxide; the sol or gel mixture is co-gelled by the addition of dilute ammonia and the resulting gel is subsequently dried, calcined, cooled, and then impregnated with a solution or solutions of at least one soluble compound of cadmium and, optionally, of thorium. As an alternate method of preparation, a hydrogel of a refractory inorganic oxide is blended with finely-divided molecular sieve material and/or pillared smectite or vermiculite clay, and a solution or solutions of at least one soluble compound of cadmium and, optionally, of thorium is added to this blend, and the resulting mixture is thoroughly blended. The blended mixture is then dried and calcined.

In still another method of preparation, the molecular sieve material and/or pillared smectite or vermiculite clay material can be pulverized into a finely-divided state and then physically admixed with a finely-divided powder of the selected refractory inorganic oxide component. After a thorough blending of the solid components, the resulting mixture can be co-pelleted, and impregnated with one or more solutions of a cadmium compound and, optionally, of a thorium compound.

It is, of course, also suitable to impregnate only one of the amorphous refractory inorganic oxide, the molecular sieve material or pillared smectite or vermiculite clay material in the mixture, or to impregnate each of the aforesaid amorphous inorganic oxide, molecular sieve material and/or pillared smectite or vermiculite clay material separately, and then to blend the inorganic oxide and molecular sieve material and/or pillared smectite or vermiculite clay material. Thus, it is contemplated that, if the catalyst employed in the method of this invention comprises an amorphous refractory inorganic oxide and at least one of a molecular sieve material and a pillared smectite or vermiculite clay material, the cadmium component can be deposited on only one, only two, or all of the components of the support. Similarly, in such cases, if a thorium component is also present in the catalyst employed in the method of this invention, the thorium component can be present with the cadmium component on the same component(s) of the support, or the cadmium component and thorium component can be on different components of the support.

It is preferred that, if the catalyst employed in the method of this invention comprises a support comprising a molecular sieve component or a pillared smectite or vermiculite clay component impregnated with the cadmium component and/or the thorium component, the impregnation of the molecular sieve component and pillared smectite or vermiculite clay component is conducted at a pH of at least about 2 in order to avoid substantial destruction of the crystallinity of the aforesaid support component. More preferably, the pH of the impregnating solution(s) in such case is from about 2.5 to about 6 in order to ensure substantial retention of the crystallinity of the aforesaid support component. Of course, the optimum pH range(s) of the impregnating solution(s) varies somewhat depending on the specific molecular sieve component and pillared smectite or vermiculite clay component employed in the preparation of a given catalyst.

In each of the above preparations involving a molecular sieve material, the molecular sieve material employed can be either in its unexchanged form or in its ion-exchanged form. Preferably, the molecular sieve material is one which has previously been cation-exchanged. A suitable cation-exchange procedure comprises making a slurry of the molecular sieve material in a solution of a cation, such as ammonium ions, which is to be exchanged with the alkali metal in the molecular sieve material, stirring the slurry at a temperature of about 100° C. for at least about 2 hours to about one week, filtering the slurry, washing the filtered solid with distilled water, and drying and calcining the solid.

It is also suitable to incorporate the precursor of the cadmium component into the molecular sieve by cation exchange using a convenient, conventional ion-exchange procedure, such as the one described generally hereinabove. Thus, the cadmium component can be incorporated into the molecular sieve support itself, in addition to or instead of being deposited on the surface of the molecular sieve support.

Suitable conditions for drying the above-described cadmium-impregnated or cadmium-exchanged supports comprise a temperature in the range of from about 90° C. to about 200° C. and a drying time of from about 0.5 to about 30 hours. Suitable calcination conditions in such methods comprise a temperature in the range of about 480° C. to about 760° C. and a calcination time of from about 2 to about 5 hours. Preferred drying and calcination conditions are a temperature of about 120° C. for about 1-2 hours and a temperature of about 538° C. for about 1-2 hours, respectively.

The general method of this invention comprises reacting an aromatic compound, water and carbon monoxide, in the presence of an aforesaid catalyst suitable for use in the method of this invention. The conditions employed in the method of this invention include a temperature in the range of from about 300° C. to about 480° C. and a pressure in the range of from about 5 to about 150 kilograms per square centimeter.

The aromatic compound employed in the method of this invention is preferably an unsubstituted or alkylated benzene or naphthalene. The mole ratio of carbon monoxide-to-water is preferably in the range of from about 1:10 to about 10:1, more preferably from about 4:1 to about 1:4, and the mole ratio of carbon monoxide-to-aromatic compound is preferably from about 10:1 to about 1:10, more preferably from about 2:1 to about 1:10. Preferably, the space velocity of the aromatic compound is from about 0.02 to about 0.5 moles of the aromatic compound per gram of catalyst per hour. It is also preferred that the reaction between the aromatic compound, water and carbon monoxide is performed at a temperature in the range of from about 315° C. to about 450° C., at a pressure in the range of from about 30 to about 100 kilograms per square centimeter. In addition, the reaction between the aromatic compound, water and carbon monoxide is preferably performed in the presence of a catalyst comprising a support comprising cadmium-exchanged zeolite Y, rare earth-exchanged zeolite Y, ultrastable zeolite Y, a pillared smectite or vermiculite clay, silica-alumina, crystalline borosilicate molecular sieve, or ZSM-5. More preferably, the catalyst support comprises crystalline borosilicate molecular sieve or ZSM-5, and in such cases, the feed is preferably benzene or toluene, and at least one of p-xylene and pseudocumene is produced. Preferably, carbon monoxide is a reactant.

The present invention will be more clearly understood from the following specific examples.

EXAMPLE 1

3000 grams of zeolite Y in the sodium form (from Union Carbide Corporation and designated LZ-Y52) was slurried in 8 liters of water, and 4000 grams of a solution of a commercially available mixture of rare earth chlorides was added to the slurry. The resulting slurry was stirred and heated at reflux for 1 hour. The solids were allowed to settle overnight and the supernatant liquid was siphoned off. The resulting solids were exchanged a second time with 4 kilograms of the mixture of rare earth chlorides in 2 liters of water, and the aforesaid stirring, refluxing, settling and siphoning steps were repeated. The resulting solids were exchanged a third time with 4 kilograms of the mixture of rare earth chlorides in 6 liters of water, and the aforesaid stirring, refluxing, settling and siphoning steps were repeated. The resulting solids were washed each 4 times with 6 liters of water, dried overnight at 120° C. and calcined for 4 hours at about 780° C.

The aforesaid triple exchange was repeated, except using instead in each exchange solution 2000 grams of the mixture of rare earth chlorides and additionally in the third exchange solution 400 grams of ammonium nitrate. The stirring, refluxing, settling, siphoning, washing and drying steps were as described for the first triple exchange.

The aforesaid triple exchange was repeated a second time, using the same steps and conditions employed in the aforesaid second triple exchange.

The final rare earth-exchanged zeolite Y demonstrated 92 percent crystallinity and contained 0.241 weight percent of sodium, 2.4 weight percent of lanthanum, 8.6 weight percent of cerium, 2.9 weight percent of neodymium, 0.20 weight percent of thorium, 1.1 weight percent of yttrium, 6.6 weight percent of aluminum and 24.8 weight percent of silicon.

50.0 grams of the resulting rare earth-exchanged zeolite Y was ground to pass a 100 mesh sieve (U.S. Series) and mixed with approximately 400 milliliters of water. The resulting mixture was blended with 512 grams of an alumina sol containing about 9.8 weight percent of alumina. 25 milliliters of an aqueous solution of ammonium hydroxide containing 28 weight percent of ammonium hydroxide was added rapidly to the resulting blend, with stirring, to gel the mixture of the rare earth-exchanged zeolite Y and alumina. The gelled material was dried at 120° C. for 40 hours. The dried material was then ground to pass a 100 mesh sieve (U.S. Series), mulled with water and extruded to a diameter of 0.2 centimeter. The extrudate was dried at 120° C. in air for 6 hours and then calcined at 540° C. in air for 6 hours. The resulting composition contained 50 weight percent of rare earth-exchanged zeolite Y and 50 weight percent of alumina.

EXAMPLE 2

A solution containing 12.6 grams of $Cd(NO_3)_2.4H_2O$ in 55 milliliters of water was combined and blended for 1 hour with 99.65 grams of the final rare earth-exchanged zeolite Y produced in Example 1 containing 50 weight percent of rare earth-exchanged zeolite Y and 50 weight percent of alumina. The blend was then dried at 120° C. for several hours and calcined at 540° C. in air for 4 hours. The resulting catalyst contained 5 weight percent of cadmium oxide, based on the weight of the catalyst.

EXAMPLE 3

30 grams of crystalline borosilicate (obtained from Amoco Chemicals Corporation and designated HAMS-1B) was suspended in sufficient water to form a sauce-like consistency and combined and blended with 219.5 grams of an alumina sol containing about 9.1 weight percent of alumina. 10 milliliters of an aqueous solution containing about 50 weight percent of ammonium hydroxide was added to the blend to gel the mixture of crystalline borosilicate and alumina. The resulting gel was dried at 120° C. in air overnight. The dried particles were ground to pass a 100 mesh sieve (U.S. Series), mulled with water, extruded to a diameter of 0.32 centimeter, dried at 120° C. overnight and calcined at 540° C. in air overnight. The resulting composition contained 60 weight percent of crystalline borosilicate HAMS-1B and 40 weight percent of alumina.

A solution containing 2.4 grams of $Cd(NO_3)_2.4H_2O$ in 8 milliliters of water was combined and blended for 1 hour with 19 grams of the aforesaid composition containing 40 weight percent of HAMS-1B. The blend was then dried at 120° C. for 1 hour and calcined at 540° C. in air for 1 hour. The resulting catalyst contained 5 weight percent of cadmium oxide, based on the weight of the catalyst.

EXAMPLE 4

A suspension of 400 grams of a bentonite, 90 weight percent of which is montmorillonite (supplied by American Colloid Company and designated Volclay 325), in 227 cubic centimeters of water was mixed with 304 grams of a 50 weight percent solution of Reheis alumina Chlorhydrol, and the pH of the resulting suspension was adjusted to 4 with ammonium hydroxide. The suspension was heated at 72° C. for 1 hour and then filtered, and the resulting separated solid was washed with water, dried at 100° C. and calcined at 500° C. for 2 hours. The resulting alumina-expanded smectite clay had a d-spacing of 16.6 angstroms as measured by X-ray diffraction. The spacing between the molecular layers of the montmorillonite was between 6 and 10 angstroms and was stable at a temperature of at least 300° C. in an air atmosphere for at least 2 hours.

30.27 grams of this composition was combined with 221.5 grams of an alumina sol containing about 9 weight percent of alumina, and 10 grams of an aqueous solution containing about 28 weight percent of ammonium hydroxide was added to gel the resulting mixture. The resulting gel was dried at 120° C. and calcined at 540° C. for 6 hours. The resulting composition contained 60 weight percent of the alumina-expanded smectite clay and 40 weight percent of alumina.

A solution containing 2.4 grams of $Cd(NO_3)_2.4H_2O$ in 8 milliliters of water was combined and blended with 19 grams of the aforesaid composition containing 60 weight percent of the alumina-expanded smectite clay and 40 weight percent of alumina. The blend was then dried at 120° C. and calcined at 540° C. for 4 hours. The resulting catalyst contained 5 weight percent of cadmium oxide, based on the weight of the catalyst.

EXAMPLES 5-9

Examples 5-9 were performed using a 300-cubic centimeter autoclave. To start a run in each of Examples 5-9, 2.0 cubic centimeters of the particular catalyst used, 2-3 cubic centimeters of toluene and, in some cases, 2 cubic centimeters of liquid water were loaded into the reactor, and the reactor was sealed. The pressure of the reactor was then raised to the desired level by introducing carbon monoxide or a mixture of carbon monoxide and either hydrogen or carbon dioxide. The temperature of the reactor was then raised to the desired level and held at that level for the desired reaction time. At the end of the reaction time, gaseous products and unreacted gaseous reactants were removed through a valve in the autoclave, trapped, and analyzed. After removal of the gaseous material, the autoclave was opened and the liquid material was removed and analyzed.

The catalyst, temperature, pressure, pressurizing gas, carbon oxide(s) and reaction time employed in each of Examples 5-9 are presented in Table 1. The composition of the organic products for each of Examples 5-9 are also presented in Table 1.

TABLE 1

| Example No. | 5 | 6 | 7 | 8 | 9 |
|---|---|---|---|---|---|
| Catalyst from Example No. | 2 | 2 | 3 | 4 | 1 |
| Toluene (cc.) | 3 | 2 | 2 | 2 | 2 |
| Water (cc.) | — | 2 | 2 | 2 | 2 |
| Temperature (°C.) | 385 | 400 | 385 | 400 | 400 |
| Reaction Time (hrs.) | 19.5 | 20.25 | 22 | 19.5 | 19.5 |
| Reaction Pressure (atm.) | 122 | 105 | 130 | 105 | 105 |
| Pressurizing Gas Composition (vol. %) | | | | | |
| CO | 33 | 85 | 85 | 85 | 85 |
| $CO_2$ | 2 | 15 | 15 | 15 | 15 |
| $H_2$ | 65 | — | — | — | — |
| Product Composition (wt. %) | | | | | |
| $C_1-C_6$ | 32.1 | 9.0 | 12.4 | 10.6 | — |
| Benzene | 3.0 | 11.5 | 17.0 | 2.0 | 34 |
| Xylenes | 41.6 | 71.0 | 52.3 | 69.4 | 66 |
| Trimethylbenzenes | 19.4 | 8.5 | 18.3 | 18.0 | — |
| Tetramethylbenzenes | 3.9 | — | — | — | — |
| Toluene Conversion (%) | 58.1 | 29.6 | 15.5 | 14.4 | 1.8 |

Example 5 is a comparative example which illustrates the method disclosed in Miller and Nevitt, copending application Ser. No. 536,672, and which employed toluene, carbon monoxide and externally supplied hydrogen as reactants. Example 9 is a comparative example which involved the use of a catalyst which did not contain a cadmium component. Examples 6-8 illustrate the method of this invention.

The results of Examples 5-9 indicate that very low reactivity results when a catalyst is used which does not contain a cadmium component. The results of Examples 5-9 also indicate that the method of this invention employing water instead of externally supplied hydrogen as a reactant is less reactive than when hydrogen is employed but affords better selectivity for the formation of xylenes than when hydrogen is employed.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A method for reacting an aromatic compound, water and carbon monoxide, at a temperature in the range of from about 300° C. to about 480° C., at a pressure in the range of from about 5 to about 150 kilograms per square centimeter, and in the presence of a catalyst composition comprising a cadmium component and a support material having acidic properties, wherein the cadmium component is in the form of the elemental metal, its oxide or salt or a combination thereof, and wherein the cadmium component is present at a concentration level in the range of from about 0.1 to about 20 weight percent, calculated as cadmium oxide and based on the weight of the catalyst, with the mole ratio of carbon monoxide-to-water being in the range of from about 4:1 to about 1:4 and with the mole ratio of carbon monoxide-to-aromatic compound being in the range of from about 2:1 to about 1:10.

2. The method of claim 1 wherein the aromatic compound is an unsubstituted or alkylated benzene or naphthalene.

3. The method of claim 1 wherein the reaction is performed at a temperature in the range of from about 315° C. to about 450° C., a pressure in the range of from about 30 to about 100 kilograms per square centimeter, a mole ratio of carbon monoxide-to-water in the range of from about 4:1 to about 1:4 and a mole ratio of carbon monoxide-to-aromatic compound in the range of from about 2:1 to about 1:10.

4. The method of claim 1 wherein the space velocity of the aromatic compound is in the range of from about 0.02 to about 0.5 moles of the aromatic compound per gram of catalyst per hour.

5. The method of claim 1 wherein the cadmium component is in the form of cadmium oxide.

6. The method of claim 1 wherein the cadmium component is present at a concentration level in the range of from about 1 to about 10 weight percent, calculated as cadmium oxide and based on the weight of the catalyst.

7. The method of claim 1 wherein the support comprises a refractory inorganic oxide, a molecular sieve, a pillared smectite or vermiculite clay, or a combination thereof.

8. The method of claim 7 wherein the refractory inorganic oxide comprises alumina, zirconia, titania, an oxide of the lanthanide series, an oxide of the actinide series, a combination thereof, or a combination thereof with silica or magnesia.

9. The method of claim 7 wherein the molecular sieve comprises a crystalline aluminosilicate or crystalline borosilicate, or a mixture thereof, in the unexchanged or cation-exchanged form.

10. The method of claim 9 wherein the crystalline aluminosilicate comprises chabazite, mordenite, erionite, clinoptilolite, zeolite A, zeolite L, zeolite X, zeolite Y, ultrastable zeolite Y, zeolite omega, ZSM-5, ZSM-11, ZSM-12, ZSM-35, ZSM-38 or ZSM-48.

11. The method of claim 10 wherein the crystalline aluminosilicate is in the hydrogen- or rare earth-exchanged form.

12. The method of claim 7 wherein the crystalline borosilicate molecular sieve comprises a molecular sieve material having the following composition in terms of mole ratios of oxides:

$$0.9 \pm 0.2 M_{2/n}O : B_2O_3 : ySiO_2 : zH_2O$$

wherein M is at least one cation having a valence of n, y is between 4 and about 600, and z is between 0 and about 160, and providing an X-ray diffraction pattern comprising the following X-ray diffraction lines and assigned strengths.

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

13. The method of claim 7 wherein the pillared smectite or vermiculite clay comprises a multiplicity of cations interposed between the molecular layers of the clay and maintaining the spacing between the molecular layers in the range of from about 6 angstroms to about 10 angstroms at a temperature of at least 300° C. in an air atmosphere for at least 2 hours.

14. The method of claim 7 wherein the support comprises from about 20 to about 95 weight percent of an aforesaid refractory inorganic oxide and from about 5 to about 80 weight percent of an aforesaid molecular sieve or pillared smectite clay.

15. The method of claim 7 wherein the support comprises cadmium-exchanged zeolite Y, rare earth-exchanged zeolite Y, ultrastable zeolite Y, a pillared smectite or vermiculite clay, silica-alumina, a crystalline borosilicate molecular sieve or ZSM-5.

16. The method of claim 15 wherein the support comprises a crystalline borosilicate molecular sieve or ZSM-5.

17. The method of claim 16 wherein the aromatic compound is benzene or toluene and at least one of p-xylene and pseudocumene is produced.

18. The method of claim 1 wherein the catalyst comprises additionally a thorium component on the support wherein the thorium component is in the form of elemental thorium, its oxide or salt or a combination thereof and is present at a concentration in the range of from about 1 to about 25 weight percent, calculated as thorium oxide and based on the weight of the catalyst.

* * * * *